(12) United States Patent
Han et al.

(10) Patent No.: US 12,369,854 B2
(45) Date of Patent: Jul. 29, 2025

(54) METHODS FOR ANALYZING BODY COMPOSITION

(71) Applicant: Olive Healthcare Inc., Seoul (KR)

(72) Inventors: Sung Ho Han, Seoul (KR); Hee Sun Hong, Seoul (KR); Byung Jic Lee, Seoul (KR)

(73) Assignee: Olive Healthcare Inc., Seoul (KR)

( * ) Notice: Subject to any disclaimer, the term of this patent is extended or adjusted under 35 U.S.C. 154(b) by 901 days.

(21) Appl. No.: 17/547,824

(22) Filed: Dec. 10, 2021

(65) Prior Publication Data

US 2023/0112030 A1 Apr. 13, 2023

(30) Foreign Application Priority Data

Oct. 7, 2021 (KR) .......................... 10-2021-0133284

(51) Int. Cl.
*A61B 5/00* (2006.01)
*A61B 5/1455* (2006.01)

(52) U.S. Cl.
CPC .......... *A61B 5/4869* (2013.01); *A61B 5/0075* (2013.01); *A61B 5/1455* (2013.01); *A61B 5/7267* (2013.01)

(58) Field of Classification Search
CPC .... A61B 5/4869; A61B 5/0075; A61B 5/7267
See application file for complete search history.

(56) References Cited

U.S. PATENT DOCUMENTS 8,280,472 B2 * 10/2012 Li ...................... A61B 5/14551
600/323
2009/0306521 A1 12/2009 Ermakov et al.
(Continued)

FOREIGN PATENT DOCUMENTS

EP 3689228 A1 8/2020
KR 1020110038020 A 4/2011
(Continued)

OTHER PUBLICATIONS

Keras Study, Advanced tools for deep learning, Chapter 7, Jan. 23, 2019 [https://subinium.github.io/Keras-7/].
(Continued)

*Primary Examiner* — Eric F Winakur
*Assistant Examiner* — Hy Khanh Doan
(74) *Attorney, Agent, or Firm* — Ryan Dean; Umberg Zipser LLP

(57) ABSTRACT

Disclosed is a method for analyzing a body component, which is performed by a computing device including at least one processor according to some exemplary embodiments of the present disclosure. The method may include: acquiring a first measurement value measured in tissue to be measured by using a first device; acquiring a chromophore concentration value measured in the tissue to be measured by using a second device different from the first device; training a neural network model by using training data generated based on the first measurement value and the chromophore concentration value; and when the training of the neural network model is completed, acquiring a prediction value of a chromophore concentration by inputting a second measurement value measured in a specific tissue by using the first device into the neural network model.

8 Claims, 10 Drawing Sheets

(56) References Cited

U.S. PATENT DOCUMENTS

| | | | |
|---|---|---|---|
| 2013/0102907 A1* | 4/2013 | Funane | A61B 5/0075 |
| | | | 600/476 |
| 2016/0296150 A1* | 10/2016 | Kostic | A61B 5/1459 |
| 2017/0071528 A1* | 3/2017 | Chen | A61B 5/0075 |
| 2020/0253561 A1 | 8/2020 | Han et al. | |
| 2021/0285909 A1 | 9/2021 | Lee et al. | |

FOREIGN PATENT DOCUMENTS

| | | |
|---|---|---|
| KR | 1020200020341 A | 2/2020 |
| KR | 102095959 B1 | 4/2020 |

OTHER PUBLICATIONS

Doronin et al., "The application of a unified Monte Carlo model in the training of artificial neural networks for the purpose of real-time in-vivo sensing of tissue optical properties," Proceeding of SPIE, vol. 10982, May 13, 2019, 8 pages.

European Patent Office, Extended European Search Report, International Application No. 21215839.8, Jun. 1, 2022, 9 pages.

Farrell et al., "The use of a neural network to determine tissue optical properties from spatially resolved diffuse reflectance measurements," Physics in Medicine & Biology, Institute of Physics Publishing, vol. 37, No. 12, Dec. 1, 1992, 6 pages.

* cited by examiner (a)

(b)

| | wv1 | wv2 | wv3 | wv4 | wv5 | wv6 | wv7 | wv8 |
|---|---|---|---|---|---|---|---|---|
| data1 | -5.7548 | -5.8069 | -5.8123 | -5.8608 | -5.9449 | -6.4786 | -6.4674 | -6.1304 |
| data2 | -5.7898 | -5.8539 | -5.8421 | -5.8993 | -5.9846 | -6.5075 | -6.4936 | -6.1508 |
| data3 | -5.8055 | -5.8692 | -5.8582 | -5.9097 | -5.9946 | -6.5267 | -6.5235 | -6.1718 |
| data4 | -5.9409 | -6.0079 | -6.0184 | -6.0633 | -6.1605 | -6.7134 | -6.7099 | -6.2841 |
| data5 | -5.9297 | -5.9920 | -6.0077 | -6.0590 | -6.1548 | -6.7026 | -6.7088 | -6.2812 |
| data6 | -5.9494 | -6.0213 | -6.0161 | -6.0717 | -6.1681 | -6.7203 | -6.7076 | -6.2851 |
| data7 | -5.8921 | -5.9910 | -6.0092 | -6.0541 | -6.1488 | -6.6790 | -6.6410 | -6.2465 |
| data8 | -5.8927 | -5.9888 | -6.0057 | -6.0425 | -6.1359 | -6.6723 | -6.6440 | -6.2466 |
| data9 | -5.8999 | -6.0014 | -6.0167 | -6.0547 | -6.1488 | -6.6816 | -6.6319 | -6.2395 |
| data10 | -5.8592 | -5.9182 | -5.9633 | -5.9598 | -6.0436 | -6.6103 | -6.5627 | -6.1941 |

61

⇕

| THC | water | lipid |
|---|---|---|
| 29.4523 | 18.1403 | 55.1449 |
| 29.4523 | 18.1403 | 55.1449 |
| 29.4523 | 18.1403 | 55.1449 |
| 32.7568 | 19.7272 | 54.7622 |
| 32.7568 | 19.7272 | 54.7622 |
| 32.7568 | 19.7272 | 54.7622 |
| 36.2123 | 19.9538 | 57.0814 |
| 36.2123 | 19.9538 | 57.0814 |
| 36.2123 | 19.9538 | 57.0814 |
| 36.1622 | 18.7129 | 59.0630 |

METHODS FOR ANALYZING BODY COMPOSITION

CROSS-REFERENCE TO RELATED APPLICATIONS

This application claims priority to and the benefit of Korean Patent Application No. 10-2021-0133284 filed in the Korean Intellectual Property Office on Oct. 07, 2021, the entire contents of which are incorporated herein by reference.

TECHNICAL FIELD

The present disclosure relates to a method for analyzing a body composition, and more particularly, to a method for acquiring a chromophore concentration value of a body tissue for analyzing a body composition by using a neural network model.

A research on the present disclosure is a research performed by receiving a support of Korea Medical Device Development Fund with a fund of a government (the Ministry of Science and ICT, the Ministry of Trade, Industry and Energy, and the Ministry of Food and Drug Safety) (project unique No. 1711138036, KMDF_PR_20200901 0053_01).

BACKGROUND ART

Recently, various techniques have been developed, which analyze a body composition of a body by using optical characteristics of a turbid medium. The techniques are attracting attention in that the techniques can provide a non-invasive and reliable body composition to the body, and a lot of interests are concentrated in research and development into a popular device according to needs of consumers.

In particular, a lot of techniques measure an absorption coefficient and a scattering coefficient of the turbid medium in a near-infrared region and calculates a concentration of chromophore included in the turbid medium to analyze the body composition of the body. In general, as a method for measuring the absorption and scattering coefficients of the turbid medium, three methods are known. Specifically, there are a continuous wave (CW) scheme of calculating a concentration of chromophore according to a multi-distance measurement scheme after making light having a constant intensity be incident on the turbid medium, a frequency-domain (FD) scheme of measuring a changed amplitude and a changed phase for a modulated light source, and a last time domain (TD) scheme of measuring a change according to a time for a pulse type light source.

Such a body composition analysis device generates a plurality of output light having different wavelengths by using LD, VCSEL, or LED as the light source, and irradiates the generated output light to a target object, and calculates the chromophore concentration by using a measurement value for light emitted from the target object.

Here, the continuous wave (CW) scheme is simple in implementation and low in cost as compared with other schemes, while has a limit in obtainable information. Meanwhile, the frequency domain or time domain scheme is high in implementation cost as compared with other schemes, while accurate information may be obtained.

For example, when a method for combining a broadband CW scheme and the frequency domain scheme is used, the chromophore concentration may be calculated at an accurate level, but this scheme is also high in implementation cost, and as a result, it is difficult to commercialize the corresponding scheme.

Accordingly, for commercialization of the scheme of analyzing the body composition of the body by measuring the chromophore concentration, there is a demand for a chromophore concentration measuring method which may be implemented easily and at low cost in the art.

Korean Patent Unexamined Publication No. "KR2011-0038020" discloses noninvasive measurement of carotenoids in biological tissue.

SUMMARY OF THE INVENTION

The present disclosure is contrived in response to the background art, and has been made in an effort to provide a method for acquiring a chromophore concentration value of a body tissue for analyzing a body composition.

However, technical objects of the present disclosure are not restricted to the technical object mentioned as above. Other unmentioned technical objects will be apparently appreciated by those skilled in the art by referencing to the following description.

An exemplary embodiment of the present disclosure provides a method for analyzing a body component, which is performed by a computing device including at least one processor. The method may include: acquiring a first measurement value measured in tissue to be measured by using a first device; acquiring a chromophore concentration value measured in the tissue to be measured by using a second device different from the first device; training a neural network model by using training data generated based on the first measurement value and the chromophore concentration value; and when the training of the neural network model is completed, acquiring a prediction value of a chromophore concentration by inputting a second measurement value measured in a specific tissue by using the first device into the neural network model.

The method may further include: generating training input data by applying a log function to the first measurement value; and generating the training data by labeling the chromophore concentration value to the training input data.

The chromophore concentration value may include at least one of a HbO2 concentration value, a HHb concentration value, a water concentration value, or a lipid concentration value.

In the training data, each of the HbO2 concentration value, the HHb concentration value, the water concentration value, and the lipid concentration value may be labeled to each of the first measurement values divided for each of the plurality of wavelength bands.

The neural network model may be trained to output a prediction value for each of the HbO2 concentration value, the HHb concentration value, the water concentration value, and the lipid concentration when the second measurement value divided for each of the plurality of wavelength bands is input.

The acquiring of the prediction value of the chromophore concentration may include inputting the second measurement value to which a log function is applied into the neural network model after applying the log function to the second measurement value, and acquiring the prediction value of the chromophore concentration value corresponding to the second measurement value from the neural network model.

The first device may include a light irradiation unit irradiating a plurality of light having different wavelengths to the tissue to be measured, and a reflection light collection unit collecting light reflected for each of a plurality of wavelengths from the tissue to be measured, and the first measurement value may be a value corresponding to the reflection light collected by the reflection light collection unit.

The second device may include at least one of a near infrared reflectance spectroscopy imaging device in which a frequency domain (FD) scheme and a broadband continuous-wave (CW) technology are fused, a frequency domain device, a time domain device, a spatially-resolved CW based device, or a device using a monte-carlo simulation or an empirical model based on a phantom experiment result.

Another exemplary embodiment of the present disclosure provides non-transitory computer readable medium including computer program, wherein the computer program. The computer program may include commands which cause a processor of a computing device to execute the following steps, and the steps may include: acquiring a first measurement value measured in tissue to be measured by using a first device; acquiring a chromophore concentration value measured in the tissue to be measured by using a second device different from the first device; training a neural network model by using training data generated based on the first measurement value and the chromophore concentration value; and when the training of the neural network model is completed, acquiring a prediction value of a chromophore concentration by inputting a second measurement value measured in a specific tissue by using the first device into the neural network model.

Technical solving means which can be obtained in the present disclosure are not limited to the aforementioned solving means and other unmentioned solving means will be clearly understood by those skilled in the art from the following description.

According to an exemplary embodiment of the present disclosure, a chromophore concentration measuring method which is simpler in implementation method and can be implemented with low cost than the existing scheme can be provided.

Effects which can be obtained in the present disclosure are not limited to the aforementioned effects and other unmentioned effects will be clearly understood by those skilled in the art from the following description.

BRIEF DESCRIPTION OF THE DRAWINGS

FIG. 8 is a flowchart for describing an example of a method for generating training data according to some exemplary embodiments of the present disclosure.

DETAILED DESCRIPTION

Figure 1:
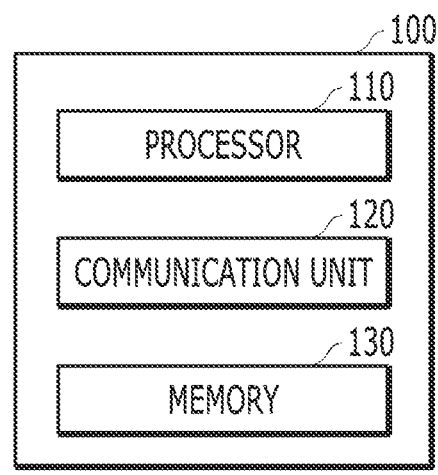
FIG. 1 is a block diagram of a computing device in which various aspects of the present disclosure may be implemented.

Various exemplary embodiments and/or aspects will be now disclosed with reference to drawings. In the following description, for the purpose of a description, multiple detailed matters will be disclosed in order to help comprehensive appreciation of one or more aspects. However, those skilled in the art of the present disclosure will recognize that the aspect(s) can be executed without the detailed matters. In the following disclosure and the accompanying drawings, specific exemplary aspects of one or more aspects will be described in detail. However, the aspects are exemplary and some of various methods in principles of various aspects may be used and the descriptions are intended to include all of the aspects and equivalents thereof. Specifically, in "embodiment", "example", "aspect", "illustration", and the like used in the specification, it may not be construed that a predetermined aspect or design which is described is more excellent or advantageous than other aspects or designs.

Various aspects and features will be presented by a system which can include one or more apparatuses, terminals, servers, devices, components, and/or modules. It should also be appreciated and recognized that various systems can include additional apparatuses, terminals, servers, devices, components, and/or modules and/or that the various systems cannot include all of apparatuses, terminals, servers, devices, components, modules, and the like discussed in association with the drawings.

"Computer program", "component", "module", "system", and the like which are terms used in this specification may be used to be compatible with each other and refer to a computer-related entity, hardware, firmware, software, and a combination of the software and the hardware, or execution of the software. For example, the component may be a processing process executed on a processor, the processor, an object, an execution thread, a program, and/or a computer, but is not limited thereto. For example, both an application executed in a computing device and the computing device may be the components. One or more components may reside within the processor and/or a thread of execution. One component may be localized in one computer. One component may be distributed between two or more computers.

The components may be executed by various computer-readable media having various data structures, which are stored therein. The components may perform communication through local and/or remote processing according to a signal (for example, data transmitted from another system through a network such as the Internet through data and/or a signal from one component that interacts with other components in a local system and a distribution system) having one or more data packets, for example.

Hereinafter, like reference numerals refer to like or similar elements regardless of reference numerals and a duplicated description thereof will be omitted. Further, in describing an exemplary embodiment disclosed in the present disclosure, a detailed description of related known technologies will be omitted if it is determined that the detailed description makes the gist of the exemplary embodiment of the present disclosure unclear. Further, the accompanying drawings are only for easily understanding the exemplary embodiment disclosed in this specification and the technical spirit disclosed by this specification is not limited by the accompanying drawings.

The terminology used in this specification is for the purpose of describing embodiments only and is not intended to limit the present disclosure. In this specification, the singular form also includes the plural form, unless the context indicates otherwise. It is to be understood that the terms "comprise" and/or "comprising" used in the specification does not exclude the presence or addition of one or more other components other than stated components.

Although the terms "first", "second", and the like are used for describing various elements or components, these elements or components are not confined by these terms, of course. These terms are merely used for distinguishing one element or component from another element or component. Therefore, a first element or component to be mentioned below may be a second element or component in a technical spirit of the present disclosure.

Unless otherwise defined, all terms (including technical and scientific terms) used in the present specification may be used as the meaning which may be commonly understood by the person with ordinary skill in the art, to which the present disclosure pertains. Terms defined in commonly used dictionaries should not be interpreted in an idealized or excessive sense unless expressly and specifically defined.

The term "or" is intended to mean not exclusive "or" but inclusive "or". That is, when not separately specified or not clear in terms of a context, a sentence "X uses A or B" is intended to mean one of the natural inclusive substitutions. That is, the sentence "X uses A or B" may be applied to any of the case where X uses A, the case where X uses B, or the case where X uses both A and B. Further, it should be understood that the term "and/or" used in this specification designates and includes all available combinations of one or more items among enumerated related items.

The terms "information" and "data" used in the specification may also be often used to be exchanged with each other.

Suffixes "module" and "unit" for components used in the following description are given or mixed in consideration of easy preparation of the specification only and do not have their own distinguished meanings or roles.

The objects and effects of the present disclosure, and technical constitutions of accomplishing these will become obvious with reference to exemplary embodiments to be described below in detail along with the accompanying drawings. In describing the present disclosure, a detailed description of known function or constitutions will be omitted if it is determined that it unnecessarily makes the gist of the present disclosure unclear. In addition, terms to be described below as terms which are defined in consideration of functions in the present disclosure may vary depending on the intention of a user or an operator or usual practice.

However, the present disclosure is not limited to exemplary embodiments disclosed below but may be implemented in various different forms. However, the exemplary embodiments are provided to make the present disclosure be complete and completely announce the scope of the present disclosure to those skilled in the art to which the present disclosure belongs and the present disclosure is just defined by the scope of the claims. Accordingly, the terms need to be defined based on contents throughout this specification.

The scope of the operations in the claims of the present disclosure arises from the functions and features described in respective steps and is not affected by the order in which respective steps in the claims are disclosed if a sequence relationship of the disclosed order in respective steps constituting the method is not specified. For example, in the claims set forth in the step including steps A and B, the scope of rights is not limited to the fact that step A precedes step B, even if step A is described before step B.

FIG. 1 is a block diagram of a computing device in which various aspects of the present disclosure may be implemented.

Referring to FIG. 1, a computing device 100 may include a processor 110, a communication unit 120, and a memory 130. However, components described above are not required in implementing the computing device 100, so the computing device 100 may have components more or less than components listed above.

The computing device 100 according to the present disclosure may be a medical related server for acquiring measurement data from a device for measuring a body composition (hereinafter, referred to as a measurement device), and analyzing the body composition based on the acquired measurement data. However, not limited thereto, but the computing device 100 may be included within the measurement device or may mean the measurement device itself.

The computing device 100 may include a predetermined type computer system or computer device such as a microprocessor, a main frame computer, a digital processor, a portable device, and a device controller. However, the present disclosure is not limited thereto.

The processor 110 of the computing device 100 generally controls an overall operation of the computing device 100. The processor 110 processes a signal, data, information, and the like input or output through the components included in the computing device 100 or drives the application program stored in the memory 130 to provide or process information or a function appropriate for the user.

The processor 110 may control at least some of the components of the computing device 100 in order to drive the application program stored in the memory 130. Furthermore, the processor 110 may combine and operate at least two of the components included in the computing device 100 in order to drive the application program.

The processor 110 of the computing device 100 may be constituted by one or more cores and may include processors for data analysis and deep learning, which include a central processing unit (CPU), a general purpose graphics processing unit (GPGPU), a tensor processing unit (TPU), and the like of the computing device. The processor 110 may read a computer program stored in the memory 130 to perform data processing for machine learning according to some exemplary embodiments of the present disclosure. According to an exemplary embodiment of the present disclosure, the processor 110 may perform a calculation for learning the neural network. The processor 110 may perform calculations for learning the neural network, which include processing of input data for learning in deep learning (DL), extracting a feature in the input data, calculating an error, updating a weight of the neural network using backpropagation, and the like. At least one of the CPU, GPGPU, and TPU of the processor 110 may process learning of a network function. For example, both the CPU and the GPGPU may process the learning of the network function and data classification using the network function. Further, in some exemplary embodiments of the present disclosure, processors of a plurality of computing devices may be used together to process the learning of the network function and the data classification using the network function. Further, the computer program executed in the computing device according to some exemplary embodiments of the present disclosure may be a CPU, GPGPU, or TPU executable program.

According to some exemplary embodiments of the present disclosure, the processor 110 of the computing device 100 trains a neural network model to acquire a prediction value of a chromophore concentration.

Specifically, the processor 110 of the computing device 100 may acquire a first measurement value measured in tissue to be measured by using a first device. Further, the processor 110 may acquire a chromophore concentration value measured in the tissue to be measured by using a second device different from the first device. Further, the processor 110 may train the neural network model by using training data generated based on the first measurement value and the chromophore concentration value. In addition, when the training of the neural network model is completed, the processor 110 the acquire the prediction value of the chromophore concentration by inputting a second measurement value measured in a specific tissue into the neural network model of which training is completed by using the first device. Here, the second measurement value may mean a measurement value for a specific tissue of which body composition analysis is required.

Hereinafter, a method for training the neural network model by the processor 110 of the computing device 100 and a method for acquiring the prediction value of the chromophore concentration by using the neural network of which training is completed will be descried below with reference to FIGS. 4 to 8.

In the present disclosure, the chromophore as an organic compound having an unsaturated bond means an atom or an atom group that absorbs light. In general, the type of chromophore which exists in the body is limited, and for example, a moisture (or water) ($H_2O$), lipid, oxygen-hemoglobin ($O_2Hb$), deoxy-hemoglobin (HHb) exists in tissues such as an arm, a leg, etc. Further, water, oxy-hemoglobin, and hemoglobin except for lipid exist in a brain.

That is, the chromophore concentration value may include at least one of a HbO2 concentration value, a HHb concentration value, a water concentration value, or a lipid concentration value. The chromophore concentration value may be used for analyzing the body composition of the body.

Hereinafter, the chromophore will be described below with reference to FIG. 2.

In the present disclosure, the first device may be driven by the continuous wave (CW) scheme of calculating the concentration of the chromophore according to the multi-distance measurement scheme after making light having a constant intensity be incident into the tissue to be measured (an exterior of the body). Relatively lower implementation cost of the first device may be required than that of the second device to be described below.

The first device may include a light irradiation unit irradiating a plurality of light having different wavelengths to the tissue to be measured, and a reflection light collection unit collecting light reflected for each of a plurality of wavelengths from the tissue to be measured. That is, the first device is constituted by a single source (light irradiation unit) and a single light detector (light collection unit) to be configured with the low cost. In addition, the first measurement value may include a value (e.g., reflectance) corresponding to the reflection light collected by the reflection light collection unit of the first device.

The light irradiation unit of the first device may include a plurality of light emitting elements constituted by a laser diode (LD), a light emitting diode (LED), or a vertical cavity surface emitting laser (VCSEL). Here, the plurality of respective light emitting elements may output output light having different wavelengths.

The reflection light collection unit of the first device may collect (or detect) the reflection light emitted from the tissue to be measured, and converts the collected reflection light into an electrical signal. Here, the reflection light may include may include light acquired by emitting the light irradiated by the light irradiation unit through the tissue to be measured. The reflection light collection unit includes at least one avalanche photodiode (APD) to amplify an AC component of the converted electrical signal. However, not limited thereto, but the reflection light collection unit may be implemented as various types including a photodiode (PD), a photo transistor, a photo multiplier tube (PMT), a photo cell, etc.

The reflection light collection unit may be disposed spaced apart from the plurality of light emitting elements included in the light irradiation unit at a predetermined distance in order to receive output light emitted from a target object.

In the present disclosure, the second device may be driven by a near infrared reflectance spectroscopy imaging scheme in which the frequency domain (FD) scheme and the broadband continuous-wave (CW) technology are fused. The relatively higher implementation cost of the second device is required than that of the first device, while the second device may acquire a high-accuracy chromophore concentration value. Further, the second device may be driven by all of the frequency domain (FD) scheme of measuring the changed amplitude and phase for the modulated light source, the time domain (TD) scheme of measuring the change according to the time for the pulse-type light source, a spatially-resolved CW based scheme, and a scheme using a monte-carlo simulation or an empirical model based on a phantom experiment result.

The second device may be, for example, a diffuse optical spectroscopic imaging (DOSI) device. Specifically, the second device may include a broadband signal generator, a driver having an input coupled to the signal generator, a light source coupled to the driver in order to expose a sample to light modulated at one or more wavelengths and one or more modulation frequencies, an optical detector including an RF switch for selectively switching an RF signal from an internal or external optical sub system in order to receive the light from the tissue to be measured, one or more circuits coupled to the optical detector in order to detecting the amplitude and/or the phase measured by the optical detector, a processor collecting data for detecting the amplitude and the phase from one or more circuits and communicating with an external host or a network computer, and a plurality of filters and amplifiers separating a signal communicated between the light detector and the amplitude and/or phase detection circuit, and interconnecting the light detector and the amplitude and/or phase detection circuit in order to increase a signal to noise ratio of the signal.

The computing device 100 according to the present disclosure may acquire a predicted value (prediction value of the chromophore concentration) to be measured by the second device by using the measurement value acquired form the first device which is relatively lower in measurement cost than the second device.

Accordingly, the computing device 100 according to the present disclosure provides the chromophore concentration measuring method which is simple in implementation method and may be implemented with the low cost to cause commercialization of a scheme of analyzing the body composition of the body by measuring the chromophore concentration.

The communication unit 120 of the computing device 100 may include one or more modules which enable communication between the computing device 100 and the first device or the second device and between the computing device 100 and the user terminal. In addition, the communication unit 120 may include one or more modules that connect the computing device 100 to one or more networks.

According to some exemplary embodiments of the present disclosure, the communication unit 120 may transmit the predicted chromophore concentration value to the user terminal. Here, a user of the user terminal may be related to a user (e.g., a doctor or a researcher) for analyzing the chromophore concentration value. However, the present disclosure is not limited thereto.

A network which connects communication between the computing device 100 and the first device and/or the second device and between the computing device 100 and the user terminal may use various wired communication systems such as public switched telephone network (PSTN), x digital subscriber line (xDSL), rate adaptive DSL (RADSL), multi rate DSL (MDSL), very high speed DSL (VDSL), universal asymmetric DSL (UADSL), high bit rate DSL (HDSL), and local area network (LAN).

The network presented here may use various wireless communication systems such as code division multi access (CDMA), time division multi access (TDMA), frequency division multi access (FDMA), orthogonal frequency division multi access (OFDMA), single carrier-FDMA (SC-FDMA), and other systems.

The network according to the exemplary embodiments of the present disclosure may be configured regardless of communication modes such as wired and wireless modes and constituted by various communication networks including a local area network (LAN), a wide area network (WAN), and the like. Further, the network may be known World Wide Web (WWW) and may adopt a wireless transmission technology used for short-distance communication, such as infrared data association (IrDA) or Bluetooth.

The techniques described in this specification may also be used in other networks in addition to the aforementioned networks.

The memory 130 of the computing device 100 may store a program for an operation of the processor 110 and temporarily or persistently store input/output data. The memory 130 may include at least one type of storage medium of a flash memory type, a hard disk type, a multimedia card micro type, a card type memory (for example, an SD or XD memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk.

According to some exemplary embodiments of the present disclosure, the memory 130 may store a neural network or a neural network structure constituting the neural network model outputting the prediction value of the chromophore concentration. Hereinafter, the neural network or the neural network structure constituting the neural network model according to the present disclosure will be described below with reference to FIG. 3.

According to software implementation, embodiments such as a procedure and a function described in the present disclosure may be implemented by separate software modules. Each of the software modules may perform one or more functions and operations described in the specification. A software code may be implemented by a software application written by an appropriate program language. The software code may be stored in the memory 130 of the computing device 100 and executed by the processor 110 of the computing device 100.

Figure 2:
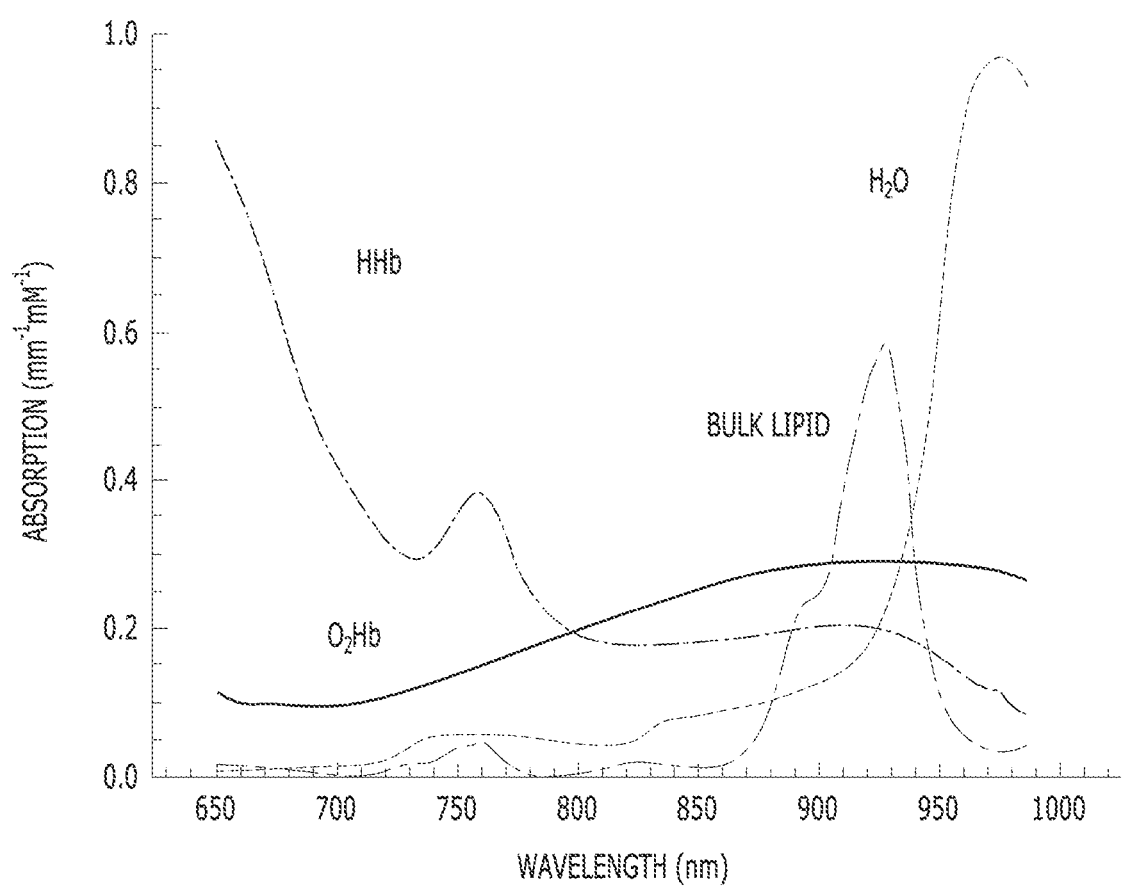
FIG. 2 is a graph illustrating an absorption spectrum of chromophores which exist in a body.

FIG. 2 is a graph illustrating an absorption spectrum of chromophores which exist in a body.

In general, the chromophores which exist in the body may have different absorption spectrum characteristics in a near infrared region.

Referring to the graph 10 illustrated in FIG. 2, water 11 has a peak characteristic in a wavelength region of approximately 980 nm and a lipid 12 has a peak characteristic in a wavelength region of approximately 930 nm. Further, oxy-hemoglobin 13 and hemoglobin 14 cross based on an isosbestic point 15 in a wavelength region of approximately 800 nm.

According to some exemplary embodiments of the present disclosure, the light irradiation unit of the first device may include light emitting elements outputting at least four wavelengths, and emit light having four discrete type wavelengths determined based on light absorption degrees of the water, the lipid, the oxy-hemoglobin, and the hemoglobin. Specifically, the discrete type wavelength emitted by each light emitting element may include a first discrete type wavelength adjacent to a peak region of the water 11 and a second discrete type wavelength adjacent to a peak region of the lipid 12, and include a third discrete type wavelength before the isosbestic point 15 of known absorption spectrums of the oxy-hemoglobin 13 and the hemoglobin 14, and a fourth discrete type wavelength of a region adjacent to the isosbestic point 15. Here, the third discrete type wavelength may be selected in a region where an absorption difference between the oxy-hemoglobin 13 and the hemoglobin 14 is large by considering the absorption degree of the hemoglobin 14. For example, the first discrete type wavelength may be approximately 975 nm and the second discrete type wavelength may be approximately 915 nm. Further, the third discrete type wavelength and the fourth discrete type wavelength may be approximately 688 nm and approximately 808 nm, respectively. However, the present disclosure is not limited thereto.

According to some exemplary embodiments of the present disclosure, the light irradiation unit of the first device may further include five, six, seven, or eight light emitting elements that further emit additional discrete type wavelengths in addition to the first to fourth discrete type wavelengths. As a result, added fifth to eighth discrete type wavelengths may be determined according to peak characteristics of other chromophores other than the chromophores (i.e., the water, the lipid, the oxy-hemoglobin, and the hemoglobin), but are not limited thereto.

For example, the first device may additionally select wavelengths of regions in which gradient degrees of the absorption spectrums of the respective chromophores are gentle, and may also additionally select wavelengths at a predetermined interval in a main region of the absorption spectrum of each chromophore.

For example, the added fifth to eighth discrete type wavelengths may be determined according to peak characteristics of absorption spectrums of collagen, melanin, methemolglobin (MetHb), CO hemoglobin (COHb), etc., in addition to the chromophores.

As another example, the added fifth to eighth discrete type wavelengths may determine based on a weight center of the absorption spectrum of the chromophores, and may be wavelengths of the 700 nm's region and/or the 800 nm's region.

The light irradiation unit of the first device according to the present disclosure may include four to eight light emitting elements as described above. However, not limited thereto, but the light irradiation unit may also include a smaller or larger number of light emitting elements by an item of a chromophore of which measurement is required or other requirements.

The first device may use both the scheme of analyzing a biological signal by using the intensity of the light reflected by irradiating the continuous wave or the frequency-domain (FD) scheme of measuring the changed amplitude and phase for the modulated light source.

Figure 3:
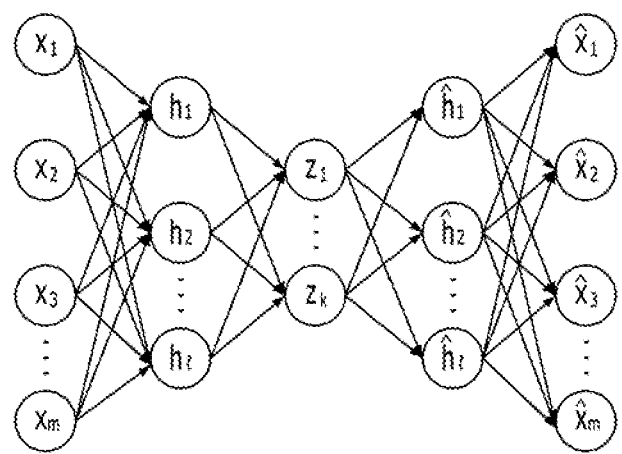
FIG. 3 is a schematic view illustrating a network function according to some exemplary embodiments of the present disclosure.

FIG. 3 is a schematic view illustrating a network function according to some exemplary embodiments of the present disclosure.

Throughout the present disclosure, a computation model, the neural network, a network function, and the neural network may be used as an interchangeable meaning. The neural network may be generally constituted by an aggregate of calculation units which are mutually connected to each other, which may be called nodes. The nodes may also be called neurons. The neural network is configured to include one or more nodes. The nodes (alternatively, neurons) constituting the neural networks may be connected to each other by one or more links.

In the neural network, one or more nodes connected through the link may relatively form the relationship between an input node and an output node. Concepts of the input node and the output node are relative and a predetermined node which has the output node relationship with respect to one node may have the input node relationship in the relationship with another node and vice versa. As described above, the relationship of the input node to the output node may be generated based on the link. One or more output nodes may be connected to one input node through the link and vice versa.

In the relationship of the input node and the output node connected through one link, a value of data of the output node may be determined based on data input in the input node. Here, a link connecting the input node and the output node to each other may have a weight. The weight may be variable and the weight is variable by a user or an algorithm in order for the neural network to perform a desired function. For example, when one or more input nodes are mutually connected to one output node by the respective links, the output node may determine an output node value based on values input in the input nodes connected with the output node and the weights set in the links corresponding to the respective input nodes.

As described above, in the neural network, one or more nodes are connected to each other through one or more links to form a relationship of the input node and output node in the neural network. A characteristic of the neural network may be determined according to the number of nodes, the number of links, correlations between the nodes and the links, and values of the weights granted to the respective links in the neural network. For example, when the same number of nodes and links exist and there are two neural networks in which the weight values of the links are different from each other, it may be recognized that two neural networks are different from each other.

The neural network may be constituted by a set of one or more nodes. A subset of the nodes constituting the neural network may constitute a layer. Some of the nodes constituting the neural network may constitute one layer based on the distances from the initial input node. For example, a set of nodes of which distance from the initial input node is n may constitute n layers. The distance from the initial input node may be defined by the minimum number of links which should be passed through for reaching the corresponding node from the initial input node. However, definition of the layer is predetermined for description and the order of the layer in the neural network may be defined by a method different from the aforementioned method. For example, the layers of the nodes may be defined by the distance from a final output node.

The initial input node may mean one or more nodes in which data is directly input without passing through the links in the relationships with other nodes among the nodes in the neural network. Alternatively, in the neural network, in the relationship between the nodes based on the link, the initial input node may mean nodes which do not have other input nodes connected through the links. Similarly thereto, the final output node may mean one or more nodes which do not have the output node in the relationship with other nodes among the nodes in the neural network. Further, a hidden node may mean nodes constituting the neural network other than the initial input node and the final output node.

In the neural network according to an exemplary embodiment of the present disclosure, the number of nodes of the input layer may be the same as the number of nodes of the output layer, and the neural network may be a neural network of a type in which the number of nodes decreases and then, increases again from the input layer to the hidden layer. Further, in the neural network according to another exemplary embodiment of the present disclosure, the number of nodes of the input layer may be smaller than the number of nodes of the output layer, and the neural network may be a neural network of a type in which the number of nodes decreases from the input layer to the hidden layer. Further, in the neural network according to yet another exemplary embodiment of the present disclosure, the number of nodes of the input layer may be larger than the number of nodes of the output layer, and the neural network may be a neural network of a type in which the number of nodes increases from the input layer to the hidden layer. The neural network according to still yet another exemplary embodiment of the present disclosure may be a neural network of a type in which the neural networks are combined.

A deep neural network (DNN) may refer to a neural network that includes a plurality of hidden layers in addition to the input and output layers. When the deep neural network is used, the latent structures of data may be determined. That is, latent structures of photos, text, video, voice, and music (e.g., what objects are in the photo, what the content and feelings of the text are, what the content and feelings of the voice are) may be determined. The deep neural network may include a convolutional neural network (CNN), a recurrent neural network (RNN), an auto encoder, generative adversarial networks (GAN), a restricted Boltzmann machine (RBM), a deep belief network (DBN), a Q network, a U network, a Siam network, a Generative Adversarial Network (GAN), and the like. The description of the deep neural network described above is just an example and the present disclosure is not limited thereto.

In an exemplary embodiment of the present disclosure, the network function may include the auto encoder. The auto encoder may be a kind of artificial neural network for outputting output data similar to input data. The auto encoder may include at least one hidden layer and odd hidden layers may be disposed between the input and output layers. The number of nodes in each layer may be reduced from the number of nodes in the input layer to an intermediate layer called a bottleneck layer (encoding), and then expanded symmetrical to reduction to the output layer (symmetrical to the input layer) in the bottleneck layer. The auto encoder may perform non-linear dimensional reduction. The number of input and output layers may correspond to a dimension after preprocessing the input data. The auto encoder structure may have a structure in which the number of nodes in the hidden layer included in the encoder decreases as a distance from the input layer increases. When the number of nodes in the bottleneck layer (a layer having a smallest number of nodes positioned between an encoder and a decoder) is too small, a sufficient amount of information may not be delivered, and as a result, the number of nodes in the bottleneck layer may be maintained to be a specific number or more (e.g., half of the input layers or more).

The neural network may be learned in at least one scheme of supervised learning, unsupervised learning, semi supervised learning, or reinforcement learning. The learning of the neural network may be a process in which the neural network applies knowledge for performing a specific operation to the neural network.

The neural network may be learned in a direction to minimize errors of an output. The learning of the neural network is a process of repeatedly inputting learning data into the neural network and calculating the output of the neural network for the learning data and the error of a target and back-propagating the errors of the neural network from the output layer of the neural network toward the input layer in a direction to reduce the errors to update the weight of each node of the neural network. In the case of the supervised learning, the learning data labeled with a correct answer is used for each learning data (i.e., the labeled learning data) and in the case of the unsupervised learning, the correct answer may not be labeled in each learning data. That is, for example, the learning data in the case of the supervised learning related to the data classification may be data in which category is labeled in each learning data. The labeled learning data is input to the neural network, and the error may be calculated by comparing the output (category) of the neural network with the label of the learning data. As another example, in the case of the unsupervised learning related to the data classification, the learning data as the input is compared with the output of the neural network to calculate the error. The calculated error is back-propagated in a reverse direction (i.e., a direction from the output layer toward the input layer) in the neural network and connection weights of respective nodes of each layer of the neural network may be updated according to the back propagation. A variation amount of the updated connection weight of each node may be determined according to a learning rate. Calculation of the neural network for the input data and the back-propagation of the error may constitute a learning cycle (epoch). The learning rate may be applied differently according to the number of repetition times of the learning cycle of the neural network. For example, in an initial stage of the learning of the neural network, the neural network ensures a certain level of performance quickly by using a high learning rate, thereby increasing efficiency and uses a low learning rate in a latter stage of the learning, thereby increasing accuracy.

In learning of the neural network, the learning data may be generally a subset of actual data (i.e., data to be processed using the learned neural network), and as a result, there may be a learning cycle in which errors for the learning data decrease, but the errors for the actual data increase. Overfitting is a phenomenon in which the errors for the actual data increase due to excessive learning of the learning data. For example, a phenomenon in which the neural network that learns a cat by showing a yellow cat sees a cat other than the yellow cat and does not recognize the corresponding cat as the cat may be a kind of overfitting. The overfitting may act as a cause which increases the error of the machine learning algorithm. Various optimization methods may be used in order to prevent the overfitting. In order to prevent the overfitting, a method such as increasing the learning data, regularization, dropout of omitting a part of the node of the network in the process of learning, utilization of a batch normalization layer, etc., may be applied.

Figure 4:
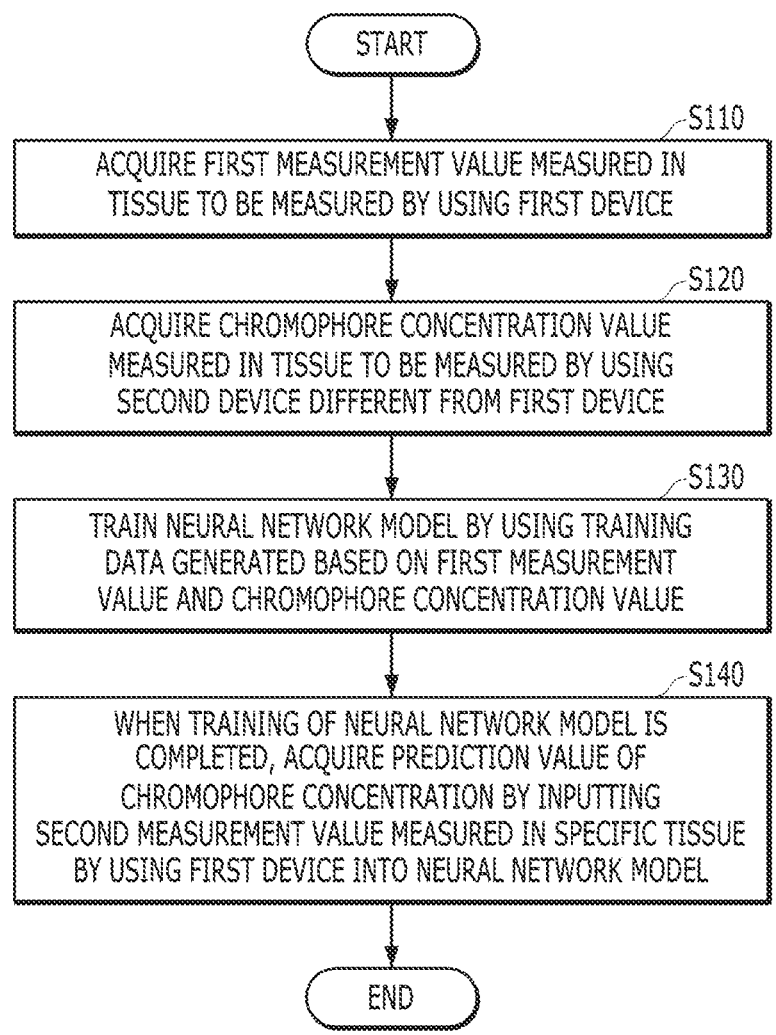
FIG. 4 is a flowchart for describing an example of a method for acquiring a prediction value of a chromophore concentration according to some exemplary embodiments of the present disclosure.

FIG. 4 is a flowchart for describing an example of a method for acquiring a prediction value of a chromophore concentration according to some exemplary embodiments of the present disclosure.

Referring to FIG. 4, a processor 110 of a computing device 100 may acquire a first measurement value measured in tissue to be measured by using a first device (S110). Here, the first measurement value may include a value for a reflectance of reflection light after irradiating specific light to the tissue to be measured.

The processor 110 may acquire a chromophore concentration value measured in the tissue to be measured by using a second device (S120). Here, the chromophore concentration value may include at least one of a HbO2 concentration value, a HHb concentration value, a water concentration value, or a lipid concentration value. The chromophore concentration value may be used for analyzing a body composition of a body.

In the present disclosure, the first device means a device which requires lower cost than the second device, but is capable of acquiring a measurement value having low accuracy. In addition, the second device means a device which requires higher cost than the first device, but is capable of acquiring a measurement value having high accuracy. Hereinafter, since the first device and the second device are described above with reference to FIG. 1, duplicated contents will be omitted.

The processor 110 of the computing device 100 may train a neural network model by using training data generated based on the first measurement value and the chromophore concentration value after acquiring the first measurement value and the chromophore concentration value (S130).

Specifically, the processor 110 of the computing device 100 may perform supervised learning of the neural network model by using the training data generated based on the first measurement value and the chromophore concentration value. More specifically, when an input value corresponding to the first measurement value is input into the neural network model, the processor 110 of the computing device 100 may perform supervised learning the neural network model so as to output an output value corresponding to the chromophore concentration value from the neural network model. However, as a method for learning the neural network model, not limited thereto, the neural network model may be learned by at lest one scheme of unsupervised learning, semi supervised learning, or reinforcement learning.

According to some exemplary embodiments of the present disclosure, the processor 110 of the computing device 100 may use a log function in order to increase accuracy of the neural network model.

Specifically, the processor 110 of the computing device 100 may generate training input data by applying the log function to the first measurement value. In addition, the processor 110 may generate the training data by labeling the chromophore concentration value to the training input data.

According to some exemplary embodiments of the present disclosure, the first measurement value to which the log function is applied my have a similar scale to the chromophore concentration value. Specifically, a relationship between the first measurement value before applying the log function and the chromophore concentration value may be expressed by a non-linear graph. Specifically, a relationship between the first measurement value to which the log function is applied and the chromophore concentration value may be expressed by a linear graph.

So that scales of the training input data and training correct answer data are similar, if the neural network model is trained with training data generated by labeling the chromophore concentration value to the training input data acquired by applying the log function to the first measurement value, the performance of the neural network model may be enhanced. For example, the accuracy of the neural network mode may be enhanced and/or a processing speed of the neural network model may be enhanced.

Hereinafter, the training data and the method for training the neural network model by the processor 110 will be described below with reference to FIGS. 5 to 8.

When the training of the neural network model is completed, the processor 110 of the computing device 100 the acquire the prediction value of the chromophore concentration by inputting a second measurement value measured in a specific tissue into the neural network model by using the first device (S140). Here, the second measurement value may mean a measurement value for a specific tissue of which body composition analysis is required.

According to the above-described method, the processor 110 of the computing device 100 may acquire a predicted value (prediction value of the chromophore concentration) to be measured by the second device by inputting the second measurement value acquired form the first device which is relatively lower in measurement cost than the second device into the trained neural network model.

Accordingly, the processor 110 of the computing device 100 provides the chromophore concentration measuring method which is simple in implementation method and may be implemented with the low cost to cause commercialization of a scheme of analyzing the body composition of the body by measuring the chromophore concentration.

Figure 5:
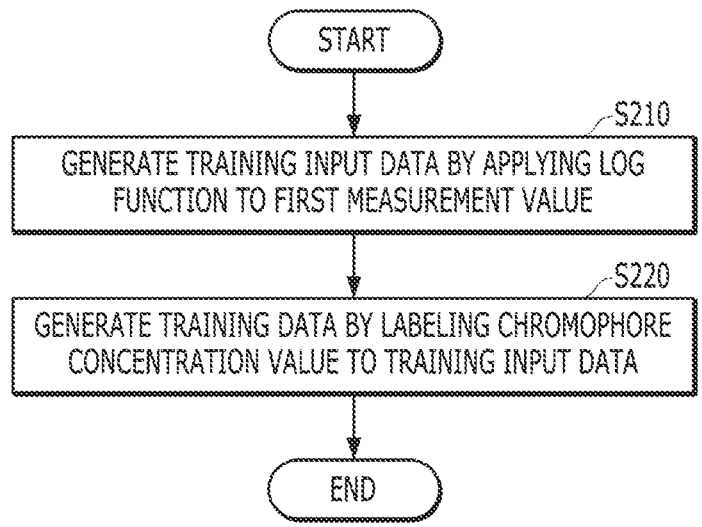
FIG. 5 is a flowchart for describing an example of a method for generating training data according to some exemplary embodiments of the present disclosure.

FIG. 5 is a flowchart for describing an example of a method for generating training data according to some exemplary embodiments of the present disclosure. FIG. 6 is a graph for describing a relationship between a chromophore concentration value, and each of a first measurement value and training input data according to some exemplary embodiments of the present disclosure. FIG. 7 is a diagram for describing a first measurement value measured in tissue to be measured by using a first device according to some exemplary embodiments of the present disclosure. FIG. 8 is a flowchart for describing an example of a method for generating training data according to some exemplary embodiments of the present disclosure.

According to some exemplary embodiments of the present disclosure, the processor 110 of the computing device 100 may train the neural network model by using the training data generating based on the first measurement value acquired from the first device and the chromophore concentration value acquired from the second device.

Here, the chromophore concentration value may include at least one of a HbO2 concentration value, a HHb concentration value, a water concentration value, or a lipid concentration value, and the first measurement value may be divided for each of a plurality of wavelength bands.

In the training data, each of the HbO2 concentration value, the HHb concentration value, the water concentration value, and the lipid concentration value may be labeled to each of the first measurement values divided for each of the plurality of wavelength bands.

In this case, when the second measurement value divided for each of the plurality of wavelength bands is input, the neural network model may be trained to output a prediction value for each of the HbO2 concentration value, each of the HHb concentration value, the water concentration value, and the lipid concentration value. For example, the neural network model may include a plurality of sub neural network models outputting only one value. The plurality of sub neural network models may include a HbO2 concentration prediction model, a HHb concentration prediction model, a water concentration prediction model, and a lipid concentration prediction model. Accordingly, the neural network model may be trained to input the second measurement value into each of the plurality of sub neural network models, and trained to output different types of concentration values from the plurality of respective sub neural network models.

As another example, the neural network model may be a model that supports multiple outputs. Accordingly, when the second measurement value is input, the neural network model may be trained to output a prediction value for each of the HbO2 concentration value, each of the HHb concentration value, the water concentration value, and the lipid concentration value. That is, the neural network model according to the present disclosure may adopt a neural network model that supports multiple inputs and multiple outputs.

Referring to FIG. 5, the processor 110 of the computing device 100 may generate training input data by applying the log function to the first measurement value in order to enhance a performance of the neural network model (S210). In addition, the processor 110 may generate the training data by labeling the chromophore concentration value to the training input data (S220).

Here, the first measurement value to which the log function is applied, and the chromophore concentration value may have a similar scale.

Figure 6A:
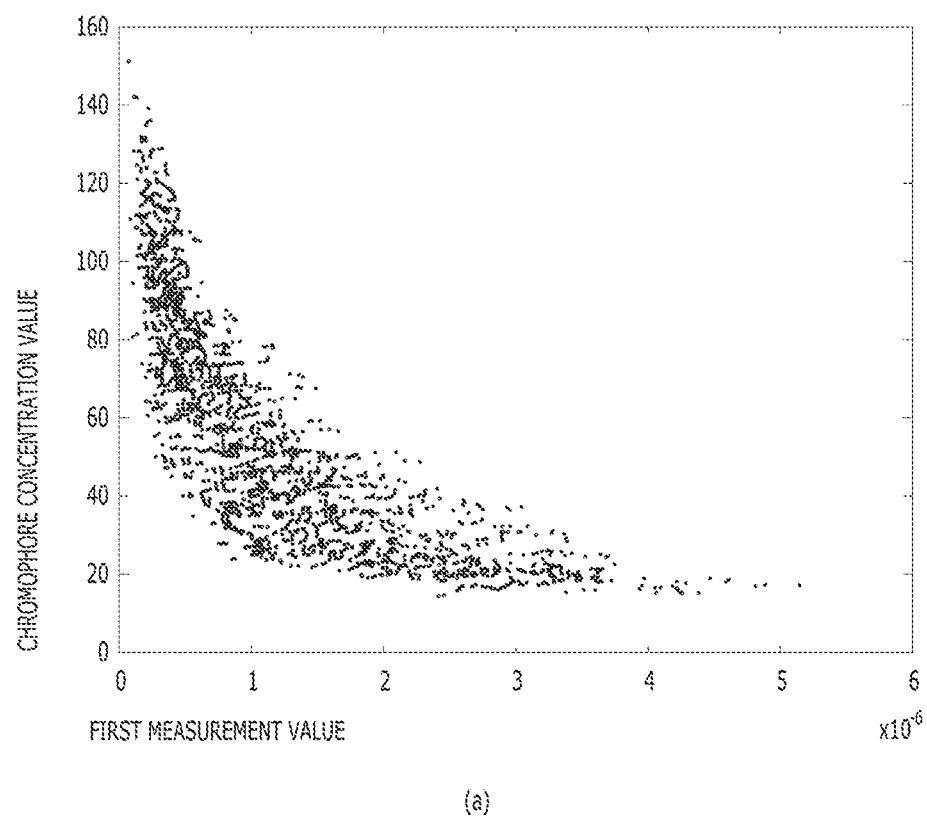
FIGS. 6A-6B are graphs for describing a relationship between a chromophore concentration value, and each of a first measurement value and training input data according to some exemplary embodiments of the present disclosure.
Figure 6B:
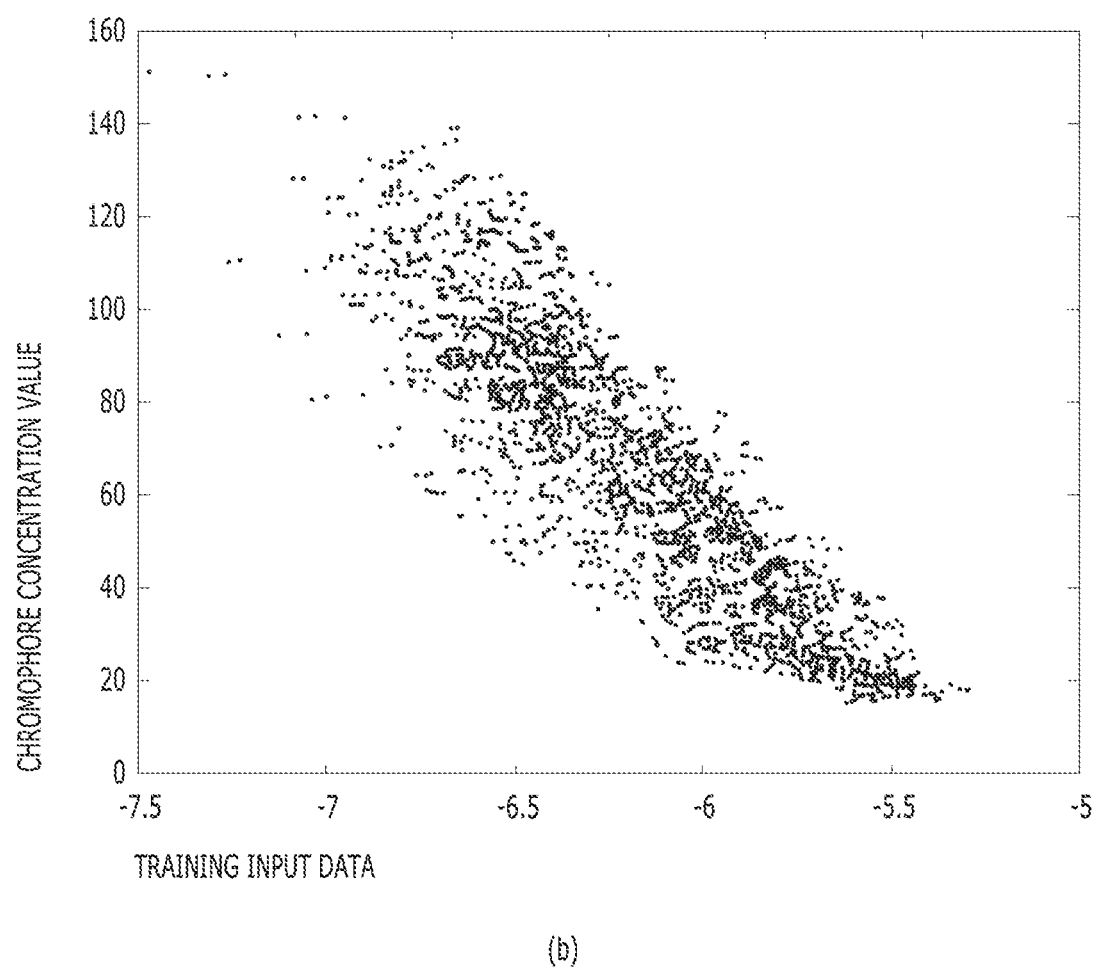
Figure 7:
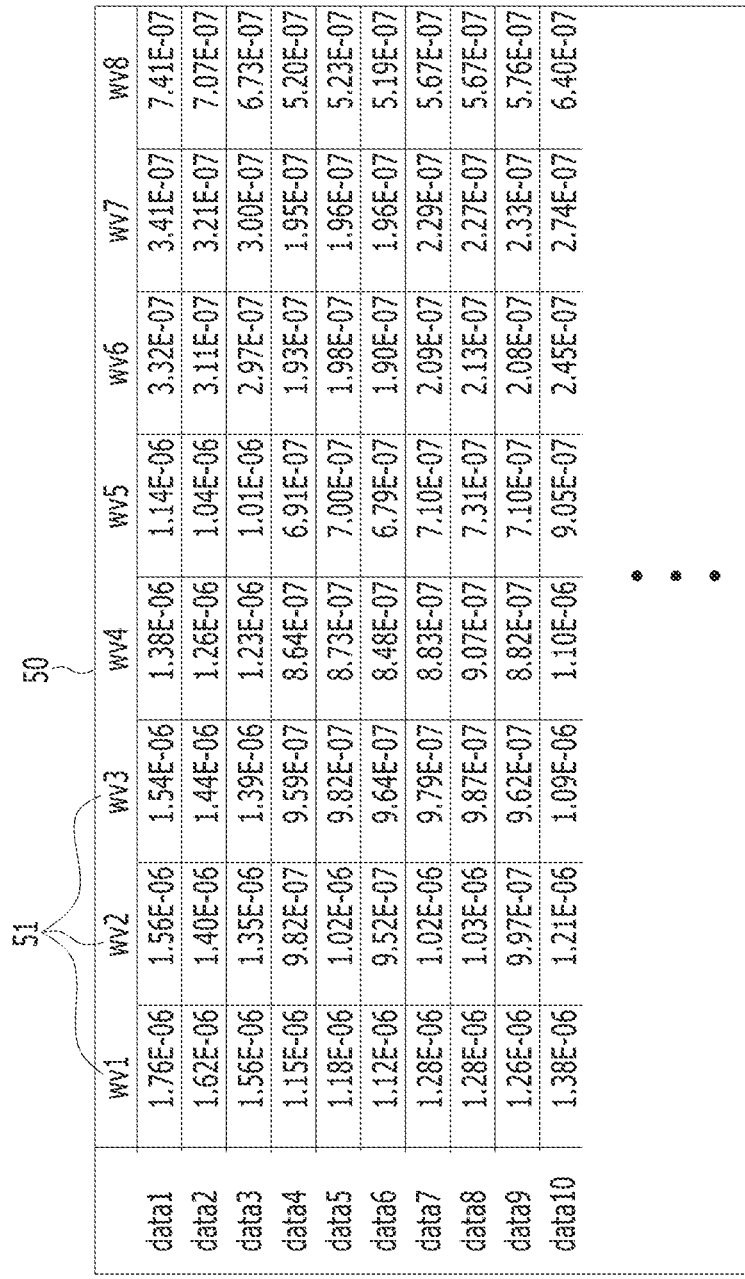
FIG. 7 is a diagram for describing a first measurement value measured in tissue to be measured by using a first device according to some exemplary embodiments of the present disclosure.

For example, referring to FIG. 6A, as illustrated, a relationship between the first measurement value and the chromophore concentration value before applying the log function may be expressed by a non-linear graph. For example, referring to FIG. 6B, as illustrated, a relationship between the first measurement value to which the log function is applied, and the chromophore concentration value may be expressed by a linear graph.

So that scales of the training input data and training correct answer data are similar, if the neural network model is trained with training data generated by labeling the chromophore concentration value to the training input data acquired by applying the log function to the first measurement value, the performance of the neural network model may be enhanced. For example, the accuracy of the neural network mode may be enhanced and/or a processing speed of the neural network model may be enhanced.

Hereinafter, an example for the method for generating the training data by the processor 110 of the computing device 100 will be described with reference to FIGS. 7 and 8.

First, referring to FIG. 7, an example of the first measurement value acquired from the first device is illustrated in a data table form. As illustrated, a first measurement value 50 expressed in the data table form may include data for each of a plurality of wavelength division values 51.

Next, referring to FIG. 8, an example of applying the log function to the first measurement value acquired from the first device (i.e., an example of the training input data) is illustrated in the data table form. As illustrated, the processor 110 of the computing device 100 may generate, as the training input data, 'log(1.76E-06)=−5.7548' acquired by applying the log function to 1.76E-06 (see FIG. 7) which is first data of a first wavelength.

The processor 110 of the computing device 100 may generate training input data by labeling a chromophore concentration value 62 to training input data 61.

Specifically, the processor 110 of the computing device 100 may generate the training data by labeling a training correct answer data set including a plurality of chromophore concentration values to a training input data set divided for each of a plurality of wavelength bands.

Accordingly, when the second measurement value divided for each of the plurality of wavelength bands is input, the neural network model may output a prediction value for each of the HbO2 concentration value, each of the HHb concentration value, the water concentration value, and the lipid concentration value. Here, the second measurement value may mean a measurement value for a specific tissue of which body composition analysis is required. In addition, the second measurement value may include values divided for each of the plurality of wavelength bands.

Figure 9:
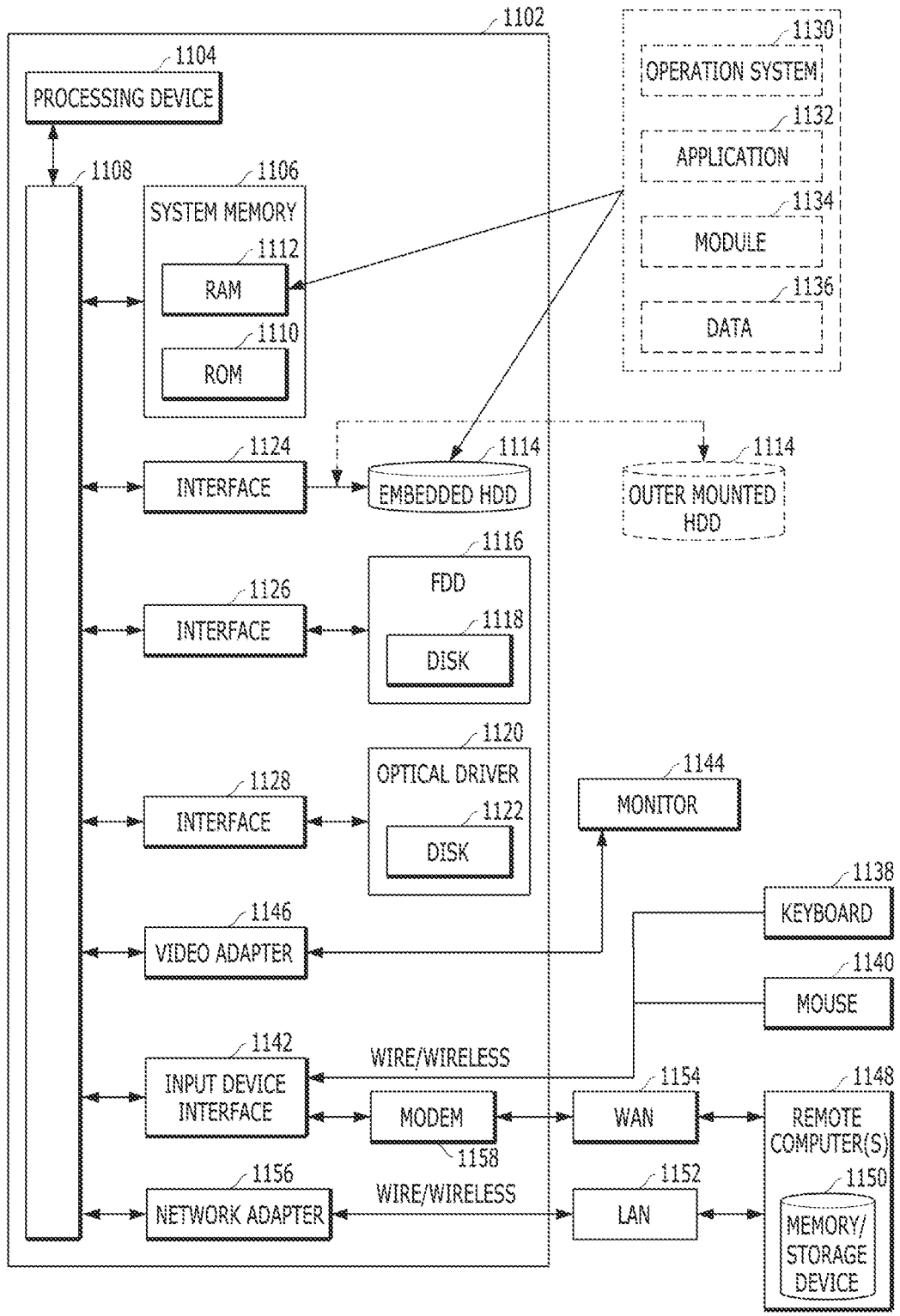
FIG. 9 is a normal and schematic view of an exemplary computing environment in which the exemplary embodiments of the present disclosure may be implemented.

FIG. 9 is a normal and schematic view of an exemplary computing environment in which the exemplary embodiments of the present disclosure may be implemented.

It is described above that the present disclosure may be generally implemented by the computing device, but those skilled in the art will well know that the present disclosure may be implemented in association with a computer executable command which may be executed on one or more computers and/or in combination with other program modules and/or as a combination of hardware and software.

In general, the program module includes a routine, a program, a component, a data structure, and the like that execute a specific task or implement a specific abstract data type. Further, it will be well appreciated by those skilled in the art that the method of the present disclosure can be implemented by other computer system configurations including a personal computer, a handheld computing device, microprocessor-based or programmable home appliances, and others (the respective devices may operate in connection with one or more associated devices as well as a single-processor or multi-processor computer system, a mini computer, and a main frame computer.

The exemplary embodiments described in the present disclosure may also be implemented in a distributed computing environment in which predetermined tasks are performed by remote processing devices connected through a communication network. In the distributed computing environment, the program module may be positioned in both local and remote memory storage devices.

The computer generally includes various computer readable media. Media accessible by the computer may be computer readable media regardless of types thereof and the computer readable media include volatile and non-volatile media, transitory and non-transitory media, and mobile and non-mobile media. As a non-limiting example, the computer readable media may include both computer readable storage media and computer readable transmission media. The computer readable storage media include volatile and non-volatile media, transitory and non-transitory media, and mobile and non-mobile media implemented by a predetermined method or technology for storing information such as a computer readable instruction, a data structure, a program module, or other data. The computer readable storage media include a RAM, a ROM, an EEPROM, a flash memory or other memory technologies, a CD-ROM, a digital video disk (DVD) or other optical disk storage devices, a magnetic cassette, a magnetic tape, a magnetic disk storage device or other magnetic storage devices or predetermined other media which may be accessed by the computer or may be used to store desired information, but are not limited thereto.

The computer readable transmission media generally implement the computer readable command, the data structure, the program module, or other data in a carrier wave or a modulated data signal such as other transport mechanism and include all information transfer media. The term "modulated data signal" means a signal acquired by setting or changing at least one of characteristics of the signal so as to encode information in the signal. As a non-limiting example, the computer readable transmission media include wired media such as a wired network or a direct-wired connection and wireless media such as acoustic, RF, infrared and other wireless media. A combination of any media among the aforementioned media is also included in a range of the computer readable transmission media.

An exemplary environment 1100 that implements various aspects of the present disclosure including a computer 1102 is shown and the computer 1102 includes a processing device 1104, a system memory 1106, and a system bus 1108. The system bus 1108 connects system components including the system memory 1106 (not limited thereto) to the processing device 1104. The processing device 1104 may be a predetermined processor among various commercial processors. A dual processor and other multi-processor architectures may also be used as the processing device 1104.

The system bus 1108 may be any one of several types of bus structures which may be additionally interconnected to a local bus using any one of a memory bus, a peripheral device bus, and various commercial bus architectures. The system memory 1106 includes a read only memory (ROM) 1110 and a random access memory (RAM) 1112. A basic input/output system (BIOS) is stored in the non-volatile memories 1110 including the ROM, the EPROM, the EEPROM, and the like and the BIOS includes a basic routine that assists in transmitting information among components in the computer 1102 at a time such as in-starting. The RAM 1112 may also include a high-speed RAM including a static RAM for caching data, and the like.

The computer 1102 also includes an interior hard disk drive (HDD) 1114 (for example, EIDE and SATA), in which the interior hard disk drive 1114 may also be configured for an exterior purpose in an appropriate chassis (not illustrated), a magnetic floppy disk drive (FDD) 1116 (for example, for reading from or writing in a mobile diskette 1118), and an optical disk drive 1120 (for example, for reading a CD-ROM disk 1122 or reading from or writing in other high-capacity optical media such as the DVD, and the like). The hard disk drive 1114, the magnetic disk drive 1116, and the optical disk drive 1120 may be connected to the system bus 1108 by a hard disk drive interface 1124, a magnetic disk drive interface 1126, and an optical disk drive interface 1128, respectively. An interface 1124 for implementing an exterior drive includes at least one of a universal serial bus (USB) and an IEEE 1394 interface technology or both of them.

The drives and the computer readable media associated therewith provide non-volatile storage of the data, the data structure, the computer executable instruction, and others. In the case of the computer 1102, the drives and the media correspond to storing of predetermined data in an appropriate digital format. In the description of the computer readable media, the mobile optical media such as the HDD, the mobile magnetic disk, and the CD or the DVD are mentioned, but it will be well appreciated by those skilled in the art that other types of media readable by the computer such as a zip drive, a magnetic cassette, a flash memory card, a cartridge, and others may also be used in an exemplary operating environment and further, the predetermined media may include computer executable commands for executing the methods of the present disclosure.

Multiple program modules including an operating system 1130, one or more application programs 1132, other program module 1134, and program data 1136 may be stored in the drive and the RAM 1112. All or some of the operating system, the application, the module, and/or the data may also be cached in the RAM 1112. It will be well appreciated that the present disclosure may be implemented in operating systems which are commercially usable or a combination of the operating systems.

A user may input instructions and information in the computer 1102 through one or more wired/wireless input devices, for example, pointing devices such as a keyboard 1138 and a mouse 1140. Other input devices (not illustrated) may include a microphone, an IR remote controller, a joystick, a game pad, a stylus pen, a touch screen, and others. These and other input devices are often connected to the processing device 1104 through an input device interface 1142 connected to the system bus 1108, but may be connected by other interfaces including a parallel port, an IEEE 1394 serial port, a game port, a USB port, an IR interface, and others.

A monitor 1144 or other types of display devices are also connected to the system bus 1108 through interfaces such as a video adapter 1146, and the like. In addition to the monitor 1144, the computer generally includes other peripheral output devices (not illustrated) such as a speaker, a printer, others.

The computer 1102 may operate in a networked environment by using a logical connection to one or more remote computers including remote computer(s) 1148 through wired and/or wireless communication. The remote computer(s) 1148 may be a workstation, a computing device computer, a router, a personal computer, a portable computer, a micro-processor based entertainment apparatus, a peer device, or other general network nodes and generally includes multiple components or all of the components described with respect to the computer 1102, but only a memory storage device 1150 is illustrated for brief description. The illustrated logical connection includes a wired/wireless connection to a local area network (LAN) 1152 and/or a larger network, for example, a wide area network (WAN) 1154. The LAN and WAN networking environments are general environments in offices and companies and facilitate an enterprise-wide computer network such as Intranet, and all of them may be connected to a worldwide computer network, for example, the Internet.

When the computer 1102 is used in the LAN networking environment, the computer 1102 is connected to a local network 1152 through a wired and/or wireless communication network interface or an adapter 1156. The adapter 1156 may facilitate the wired or wireless communication to the LAN 1152 and the LAN 1152 also includes a wireless access point installed therein in order to communicate with the wireless adapter 1156. When the computer 1102 is used in the WAN networking environment, the computer 1102 may include a modem 1158 or has other means that configure communication through the WAN 1154 such as connection to a communication computing device on the WAN 1154 or connection through the Internet. The modem 1158 which may be an internal or external and wired or wireless device is connected to the system bus 1108 through the serial port interface 1142. In the networked environment, the program modules described with respect to the computer 1102 or some thereof may be stored in the remote memory/storage device 1150. It will be well known that an illustrated network connection is exemplary and other means configuring a communication link among computers may be used.

The computer 1102 performs an operation of communicating with predetermined wireless devices or entities which are disposed and operated by the wireless communication, for example, the printer, a scanner, a desktop and/or a portable computer, a portable data assistant (PDA), a communication satellite, predetermined equipment or place associated with a wireless detectable tag, and a telephone. This at least includes wireless fidelity (Wi-Fi) and Bluetooth wireless technology. Accordingly, communication may be a predefined structure like the network in the related art or just ad hoc communication between at least two devices.

The wireless fidelity (Wi-Fi) enables connection to the Internet, and the like without a wired cable. The Wi-Fi is a wireless technology such as the device, for example, a cellular phone which enables the computer to transmit and receive data indoors or outdoors, that is, anywhere in a communication range of a base station. The Wi-Fi network uses a wireless technology called IEEE 802.11(a, b, g, and others) in order to provide safe, reliable, and high-speed wireless connection. The Wi-Fi may be used to connect the computers to each other or the Internet and the wired network (using IEEE 802.3 or Ethernet). The Wi-Fi network may operate, for example, at a data rate of 11 Mbps (802.11a) or 54 Mbps (802.11b) in unlicensed 2.4 and 5 GHz wireless bands or operate in a product including both bands (dual bands).

It will be appreciated by those skilled in the art that information and signals may be expressed by using various different predetermined technologies and techniques. For example, data, instructions, commands, information, signals, bits, symbols, and chips which may be referred in the above description may be expressed by voltages, currents, electromagnetic waves, magnetic fields or particles, optical fields or particles, or predetermined combinations thereof.

It may be appreciated by those skilled in the art that various exemplary logical blocks, modules, processors, means, circuits, and algorithm steps described in association with the exemplary embodiments disclosed herein may be implemented by electronic hardware, various types of programs or design codes (for easy description, herein, designated as software), or a combination of all of them. In order to clearly describe the intercompatibility of the hardware and the software, various exemplary components, blocks, modules, circuits, and steps have been generally described above in association with functions thereof Whether the functions are implemented as the hardware or software depends on design restrictions given to a specific application and an entire system. Those skilled in the art of the present disclosure may implement functions described by various methods with respect to each specific application, but it should not be interpreted that the implementation determination departs from the scope of the present disclosure.

Various exemplary embodiments presented herein may be implemented as manufactured articles using a method, a device, or a standard programming and/or engineering technique. The term manufactured article includes a computer program, a carrier, or a medium which is accessible by a predetermined computer-readable storage device. For example, a computer-readable storage medium includes a magnetic storage device (for example, a hard disk, a floppy disk, a magnetic strip, or the like), an optical disk (for example, a CD, a DVD, or the like), a smart card, and a flash memory device (for example, an EEPROM, a card, a stick, a key drive, or the like), but is not limited thereto. Further, various storage media presented herein include one or more devices and/or other machine-readable media for storing information.

It will be appreciated that a specific order or a hierarchical structure of steps in the presented processes is one example of exemplary accesses. It will be appreciated that the specific order or the hierarchical structure of the steps in the processes within the scope of the present disclosure may be rearranged based on design priorities. Appended method claims provide elements of various steps in a sample order, but the method claims are not limited to the presented specific order or hierarchical structure.

The description of the presented embodiments is provided so that those skilled in the art of the present disclosure use or implement the present disclosure. Various modifications of the exemplary embodiments will be apparent to those skilled in the art and general principles defined herein can be applied to other exemplary embodiments without departing from the scope of the present disclosure. Therefore, the present disclosure is not limited to the exemplary embodiments presented herein, but should be interpreted within the widest range which is coherent with the principles and new features presented herein.

What is claimed is:

1. A method for analyzing a body component, which is performed by a computing device including at least one processor, the method comprising:
   acquiring a first measurement value measured in tissue to be measured by using a first device operating according to a continuous-wave scheme;
   acquiring a chromophore concentration value measured in the tissue to be measured by using a second device operating according to a different scheme from the first device;
   training a neural network model by using training data generated based on the first measurement value and the chromophore concentration value; and
   when the training of the neural network model is completed, acquiring a prediction value of a chromophore concentration by inputting a second measurement value measured in a specific tissue by using the first device into the neural network model,
   wherein the second device includes at least one of a near infrared reflectance spectroscopy imaging device in which a frequency domain scheme and a broadband continuous-wave technology are fused, a frequency domain device, a time domain device, a spatially-resolved continuous-wave based device, or a device using a monte-carlo simulation or an empirical model based on a phantom experiment result.

2. The method of claim 1, further comprising:
   generating training input data by applying a log function to the first measurement value; and
   generating the training data by labeling the chromophore concentration value to the training input data.

3. The method of claim 2, wherein the chromophore concentration value includes at least one of a HbO2 concentration value, a HHb concentration value, a water concentration value, or a lipid concentration value.

4. The method of claim 3, wherein in the training data, each of the HbO2 concentration value, the HHb concentration value, the water concentration value, and the lipid concentration value is labeled to each of the first measurement values divided for each of a plurality of wavelength bands.

5. The method of claim 4, wherein the neural network model is trained to output a prediction value for each of the HbO2 concentration value, the HHb concentration value, the water concentration value, and the lipid concentration when the second measurement value divided for each of the plurality of wavelength bands is input.

6. The method of claim 2, wherein the acquiring of the prediction value of the chromophore concentration includes
   inputting the second measurement value to which a log function is applied into the neural network model after applying the log function to the second measurement value, and
   acquiring the prediction value of the chromophore concentration value corresponding to the second measurement value from the neural network model.

7. The method of claim 1, wherein the first device includes a light irradiation unit irradiating a plurality of light having different wavelengths to the tissue to be measured, and a reflection light collection unit collecting light reflected for each of a plurality of wavelengths from the tissue to be measured, and
   the first measurement value is a value corresponding to the reflection light collected by the reflection light collection unit.

8. A non-transitory computer readable medium including computer program, wherein the computer program includes commands which cause a processor of a computing device to execute the following steps, the steps comprising:
   acquiring a first measurement value measured in tissue to be measured by using a first device operating according to a continuous-wave scheme;
   acquiring a chromophore concentration value measured in the tissue to be measured by using a second device operating according to a different scheme from the first device;
   training a neural network model by using training data generated based on the first measurement value and the chromophore concentration value; and
   when the training of the neural network model is completed, acquiring a prediction value of a chromophore concentration by inputting a second measurement value measured in a specific tissue by using the first device into the neural network model,
   wherein the second device includes at least one of a near infrared reflectance spectroscopy imaging device in which a frequency domain scheme and a broadband continuous-wave technology are fused, a frequency domain device, a time domain device, a spatially-resolved continuous-wave based device, or a device using a monte-carlo simulation or an empirical model based on a phantom experiment result.

* * * * *